(12) United States Patent
Siccardi et al.

(10) Patent No.: US 10,893,952 B2
(45) Date of Patent: Jan. 19, 2021

(54) INTERVERTEBRAL FUSION CAGE

(71) Applicant: MEDACTA INTERNATIONAL SA, Castel San Pietro (CH)

(72) Inventors: Francesco Siccardi, Castel San Pietro (CH); Meinrad Fiechter, Castel San Pietro (CH); Matteo Metzger, Castel San Pietro (CH); Marco Riva, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 144 days.

(21) Appl. No.: 16/343,446

(22) PCT Filed: Oct. 16, 2017

(86) PCT No.: PCT/IB2017/056411
§ 371 (c)(1),
(2) Date: Apr. 19, 2019

(87) PCT Pub. No.: WO2018/073724
PCT Pub. Date: Apr. 26, 2018

(65) Prior Publication Data
US 2019/0274842 A1  Sep. 12, 2019

(30) Foreign Application Priority Data
Oct. 20, 2016  (IT) .......................... 102016000105751

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/447* (2013.01); *A61F 2/4425* (2013.01);
(Continued)

(58) Field of Classification Search
CPC ..... A61F 2/4611; A61F 2/4455; A61F 2/4425
See application file for complete search history.

(56) References Cited

U.S. PATENT DOCUMENTS 5,258,031 A * 11/1993 Salib .................... A61F 2/4425
                                               623/17.15
6,395,031 B1 * 5/2002 Foley .................... A61F 2/4465
                                               623/17.11
(Continued)

FOREIGN PATENT DOCUMENTS

JP  2008-507363 A  3/2008
JP  2014-507167 A  3/2014
(Continued)

OTHER PUBLICATIONS

English Translation of Notice of Reasons for Refusal issued in JP 2019-520974, dated Mar. 5, 2020.
(Continued)

*Primary Examiner* — Christian A Sevilla
(74) *Attorney, Agent, or Firm* — Meunier Carlin & Curfman LLC

(57) ABSTRACT

An intervertebral fusion cage for the fusion of two vertebral bodies of the vertebral column comprises a first portion and a second portion opposite the first, both having a planar conformation axially elongated along a central axis. The first and the second portion have respective contact surfaces for receiving, in abutment, a respective vertebral body. The cage can also comprise a gripping area for connection with a positioning device. The first and the second portion are hinged to each other along a hinge axis so as to be able to rotate relatively in relation to each other with a continuous movement.

15 Claims, 6 Drawing Sheets

(52) U.S. Cl.
CPC .......... *A61F 2/4465* (2013.01); *A61F 2/4611* (2013.01); *A61F 2002/30182* (2013.01); *A61F 2002/30187* (2013.01); *A61F 2002/30322* (2013.01); *A61F 2002/30405* (2013.01); *A61F 2002/30471* (2013.01); *A61F 2002/30538* (2013.01); *A61F 2002/30593* (2013.01); *A61F 2002/30622* (2013.01); *A61F 2002/30843* (2013.01)

(56) References Cited

U.S. PATENT DOCUMENTS

| | | | |
|---|---|---|---|
| 6,685,742 B1 | 2/2004 | Jackson | |
| 8,496,706 B2 * | 7/2013 | Ragab | A61F 2/447 623/17.11 |
| 2004/0186577 A1 | 9/2004 | Ferree | |
| 2005/0113916 A1 | 5/2005 | Branch | |
| 2008/0300685 A1 * | 12/2008 | Carls | A61F 2/442 623/17.11 |
| 2012/0109319 A1 | 5/2012 | Perisic | |
| 2016/0015522 A1 * | 1/2016 | Arnin | A61F 2/4425 623/17.15 |

FOREIGN PATENT DOCUMENTS

| | | |
|---|---|---|
| JP | 2014-512883 A | 5/2014 |
| WO | 2006/012592 A1 | 2/2006 |
| WO | 2011/007240 A1 | 1/2011 |
| WO | 2012/047712 A1 | 4/2012 |
| WO | 2012/112196 A1 | 8/2012 |
| WO | 2016/040125 A1 | 3/2016 |
| WO | WO-2016040125 A1 * | 3/2016 ........... A61F 2/4455 |
| WO | 2016/057940 A1 | 4/2016 |

OTHER PUBLICATIONS

English Translation of Decision of Refusal issued in JP 2019/520974, dated Jul. 14, 2020.
International Search Report and Written Opinion. Issued by the European Patent Office in Application No. PCT/IB2017/056411 dated Jan. 4, 2018. 13 pages.

* cited by examiner

INTERVERTEBRAL FUSION CAGE

The present invention relates to a fusion cage for the fusion of two vertebrae.

Such implants have been used successfully, for decades, in the field of surgery in treating spinal pathologies, wherein the fusion of two adjacent vertebral bodies is made necessary, such as, for example, fractured vertebrae, deformities of the vertebral column, spinal instability or weakness, spondylolisthesis, spinal disc herniation, chronic low back pain and others.

Intervertebral surgical implants are known in the prior art comprising a central body, said fusion cage suitable for being inserted into the intervertebral space by means of a special insertion instrument.

These cages have an elongated conformation and present two supporting surfaces suitable for receiving the vertebral bodies. Cages are used with parallel contact surfaces when the patient does not require any correction of the spinal curvature. Consequently, in this case, the fusion cage will present an axial development substantially similar to the dimension characteristic of the body of the vertebra resting upon it. After inserting the fusion cage into the intervertebral space, the two vertebrae beside the fusion cage will be arranged parallel to each other, thus locked and unable to move.

If the curvature of the patient's vertebral column requires correction, the prior art suggests choosing a fusion cage with non-parallel contact surfaces, presenting an inclination angle between them with a default value. Consequently, by inserting such fusion cage inside the intervertebral space and forcing the vertebrae to make contact with the contact surfaces of the fusion cage, it is possible to impose a correction with a set value on the curvature of the spine.

However, by using such fusion cages, the correction angle imposed on the spinal curvature is fixed, as it is imposed by the inclination of the chosen fusion cage. An attempt has been made to vary said correction angle by using a fusion cage smaller than that required by the patient's anatomy. In this way, the fusion cage is inserted into the intervertebral space taking up only a part of the space. Depending on whether it is necessary to give the patient's spine a greater or smaller correction angle in relation to the one guaranteed by the fusion cage, the latter is inserted more or less deeply, consequently ensuring an empirical variation of the correction angle. The empiricity of the variation of the correction angle guaranteed by the method described above, cannot guarantee that the spinal curvature is corrected sufficiently, with the risk of creating further damage to the patient's bone structure.

Furthermore, the placing of a vertebral body on a fusion cage whose dimensions are not optimal creates a concentration of mechanical stress in the areas of the placed vertebral body around the edges of the fusion cage. This concentration of mechanical stress may damage the bone structure of the vertebra, which can lead to the formation of cracks and possible breakages.

To overcome these inconveniences, fusion cages are used with an inclination angle variable between default values. The option of varying the inclination angle gives the surgeon the possibility to choose the inclination angle of the fusion cage closest to the correction angle needed to restore the correct curvature of the patient's spine.

However, fusion cages with a variable inclination angle known in the state-of-the-art, do not allow any inclination angle to be chosen; the surgeon can only choose an angle from a range of predetermined angles. This happens because the relative movement between the contact surfaces able to determine the inclination angle is discrete.

Consequently, as it is impossible to choose any value of the inclination angle within the interval foreseen by the fusion cage, the surgeon must choose the inclination angle, which is closest to the correction value required for the patient. It is evident how this limitation implies an unorthodox alignment of the spine to the natural curvature of the same. The present invention overcomes the inconveniences of what is known in the state-of-the-art, by providing an intervertebral fusion cage that allows the surgeon to choose the correct inclination angle, aimed at reconstructing the natural curvature of the patient's spine. This is made possible by the characteristic in claim 1. In fact, thanks to a relative continuous movement between the two contact surfaces of the intervertebral fusion cage, the inclination angle can be varied at will during the operating phase until reaching the inclination angle corresponding to a perfect re-alignment of the curvature of the vertebral column with what is naturally foreseen. After placing the intervertebral fusion cage between two vertebrae, the surgeon will manipulate the bone structure to reconstruct the correct curvature of the vertebral column, seeing his movements assisted by the continual variation of the inclination angle of the fusion cage.

This feature minimises the stress transmitted to the vertebrae during the operations of inserting the fusion cage, avoiding possible damage to the bone structure.

Furthermore, depending on the direction of insertion of the fusion cage in relation to the patient's vertebral column, it will be possible to correct every type of misalignment of the patient's bone structure. For example, it will be possible to intervene in the case of both lordosis, kyphosis and scoliosis. The particular conformation of the side profile, so-called "projectile", combined with the relative continuous movement between the contact surfaces of the intervertebral fusion cage offers quick and easy insertion of said fusion cage in the intervertebral space, making the implantation quick and easy and avoiding possible damage to the vertebral bone structure. The advantageous positioning of the hinge axis, which allows the relative continuous movement of the contact surfaces of the fusion cage, makes the present invention particularly suitable for minimally invasive surgical operations, where the surgeon's manoeuvring space is limited, and the visibility of the operating field reduced due to the presence of bodily fluids, neural elements, blood vessels and bone structures.

Further features and advantages of the intervertebral fusion cage according to the invention will become more apparent from the subsequent description provided here, of various embodiments described by way of example, which are non-limiting, with reference to the accompanying drawings, wherein.

An example of an intervertebral fusion cage is illustrated in the accompanying figures according to the present invention.

The intervertebral fusion cage is interposed between two consecutive vertebrae to reconstruct the spinal continuity in the case of fractures of the spine.

The intervertebral fusion cage, the subject of the present invention, comprises a first portion 2 and a second 3 portion, opposite the first 2, both having a substantially planar conformation.

The first 2 and the second 3 portion have a substantially identical planar form.

In the embodiments in FIGS. 1-8, the first 2 and the second 3 portion are axially elongated along a central axis 1a.

Figure 9:
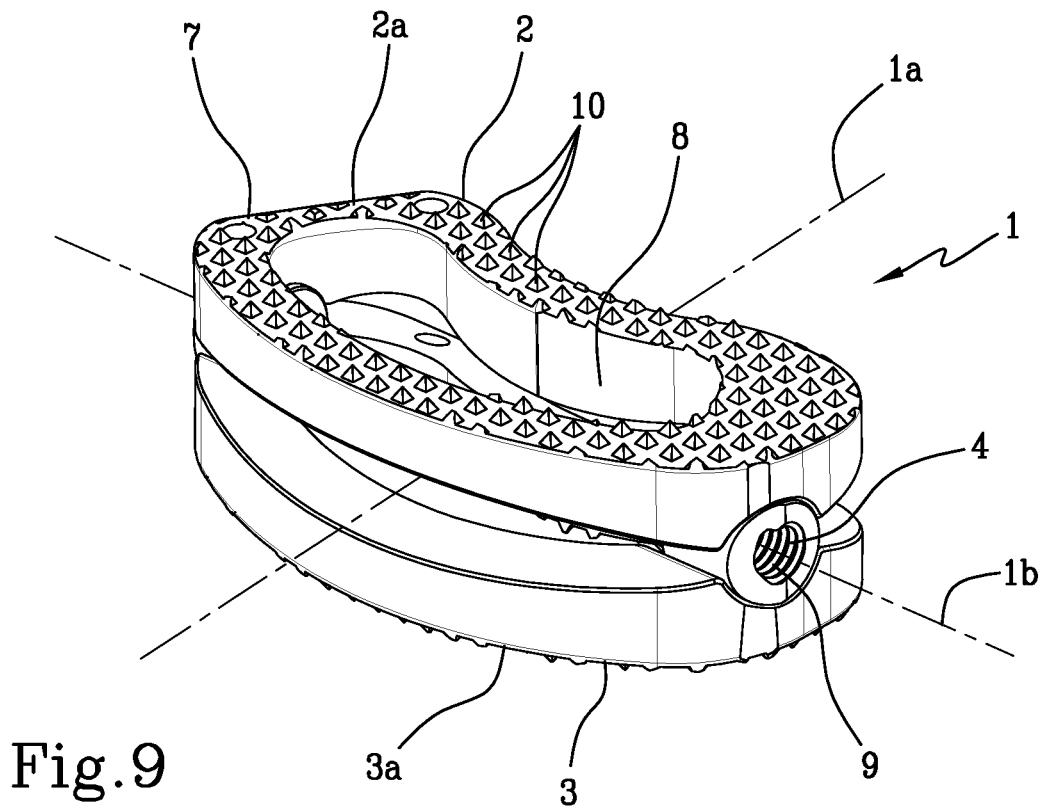
Figure 10:
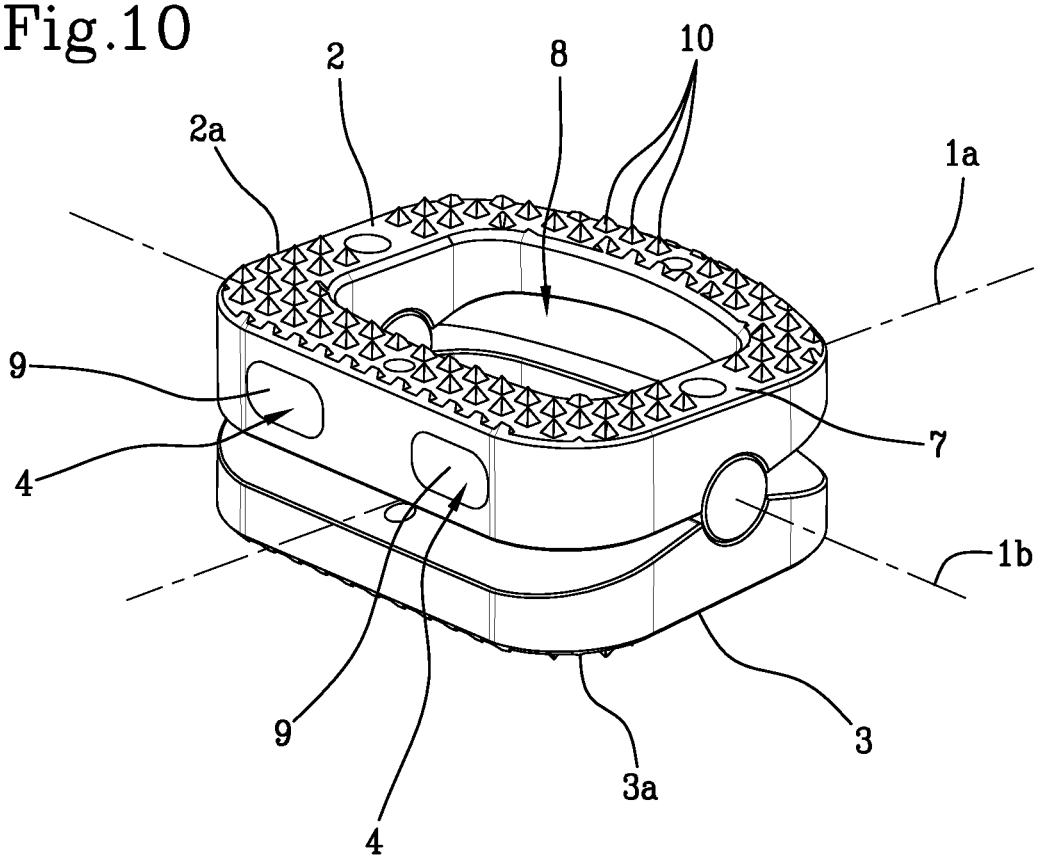
Figure 11:
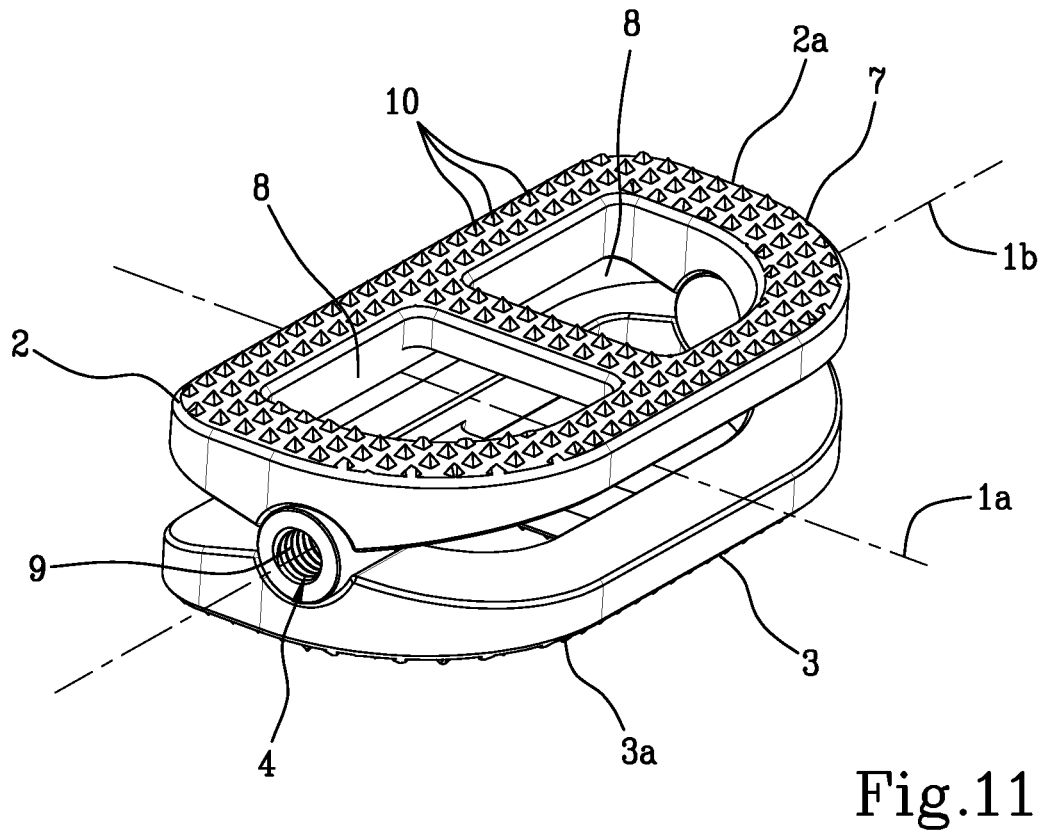

Whereas, in the conformations in FIGS. 9-11, the first 2 and the second 3 portion are elongated along a hinge axis 1b, which is transversal and, more specifically, orthogonal to the central axis 1a.

Each portion 2 and 3 presents a respective contact surface 2a and 3a suitable for receiving, in abutment, a respective vertebral body.

Such contact surfaces 2a and 3a are facing outwards in relation to the cage 1 itself, each presenting a plurality of projections 10 to increase the grip on the vertebral body.

In fact, once the cage has been inserted between two consecutive vertebrae, it is necessary to make the spine adopt its natural curvature: in this phase, as it is necessary to manipulate the bone structure, there is a risk of misalignment between the cage and the vertebral column. A rough surface or a surface with a plurality of protrusions, preferably sharp, increases the grip, preventing the cage from slipping between the vertebrae and adopting an incorrect position.

Such protrusions are preferably sharp projections, for example shaped like a pyramid.

The first 2 and the second 3 portion are hinged to each other along a hinge axis 1b, so as to be able to rotate relatively in relation to each other with a continuous movement, allowing the first 2 and the second 3 portion to incline relatively, in relation to each other, following the natural inclination angle of the spine.

The rotation angle α of the first portion 2 relatively in relation to the second portion 3 is comprised between 0° and 40°, preferably between 0° and 30°. The cage according to the embodiments shown in FIGS. 9-11 can also rotate according to a negative angle: in this case, the angle α is comprised between −40° and +40°, preferably between −30° and +30°.

In some embodiments, illustrated by way of example in FIGS. 7-11, the hinge axis 1b lies perpendicularly to the central axis 1a of the cage 1. Alternatively, as illustrated in FIGS. 1-6, the hinge axis 1b can be arranged differently angled in relation to the central axis 1a. It must be noted, however, that in all embodiments of the present invention, the hinge axis is perpendicular to the sagittal plane of the patient's body, when the cage is implanted.

In the present description, as in the accompanying claims, the term "sagittal plane" is understood to mean a plane that runs in an anterior-posterior direction and divides the patient's body into two parts, right and left.

Figure 1:
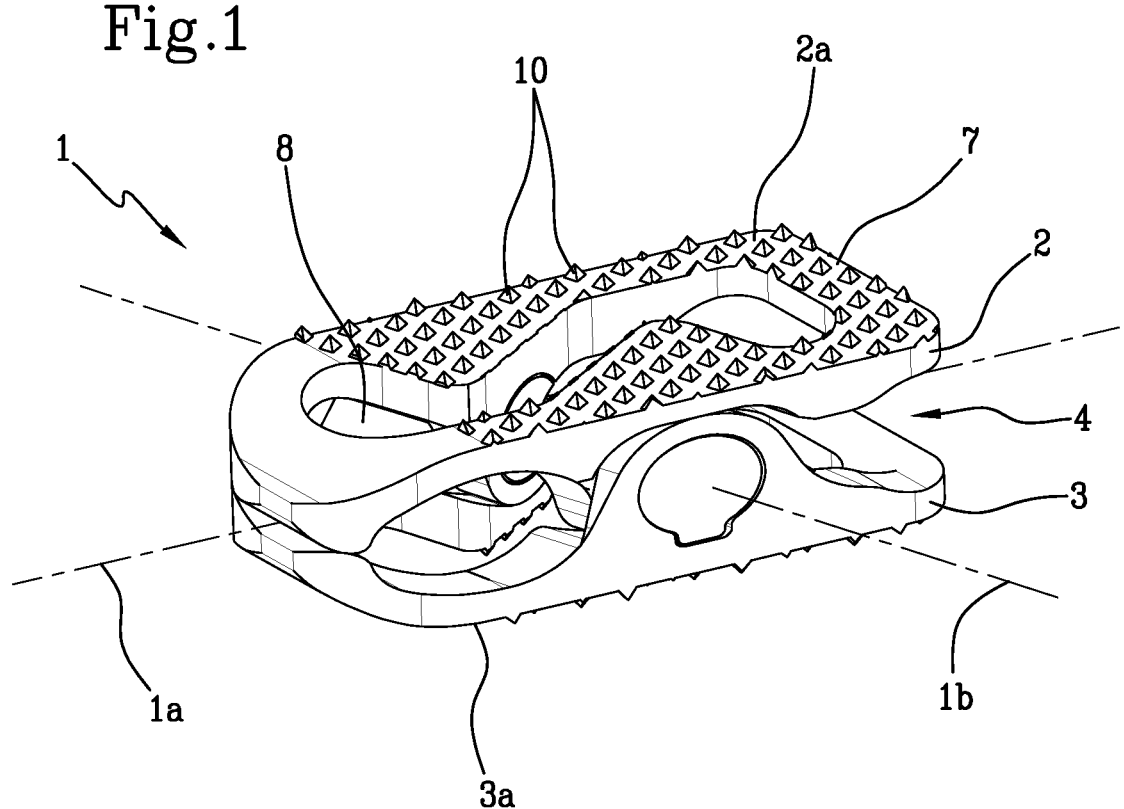
FIG. 1 is a frontal perspective view of an intervertebral fusion cage according to the present invention.
Figure 2:
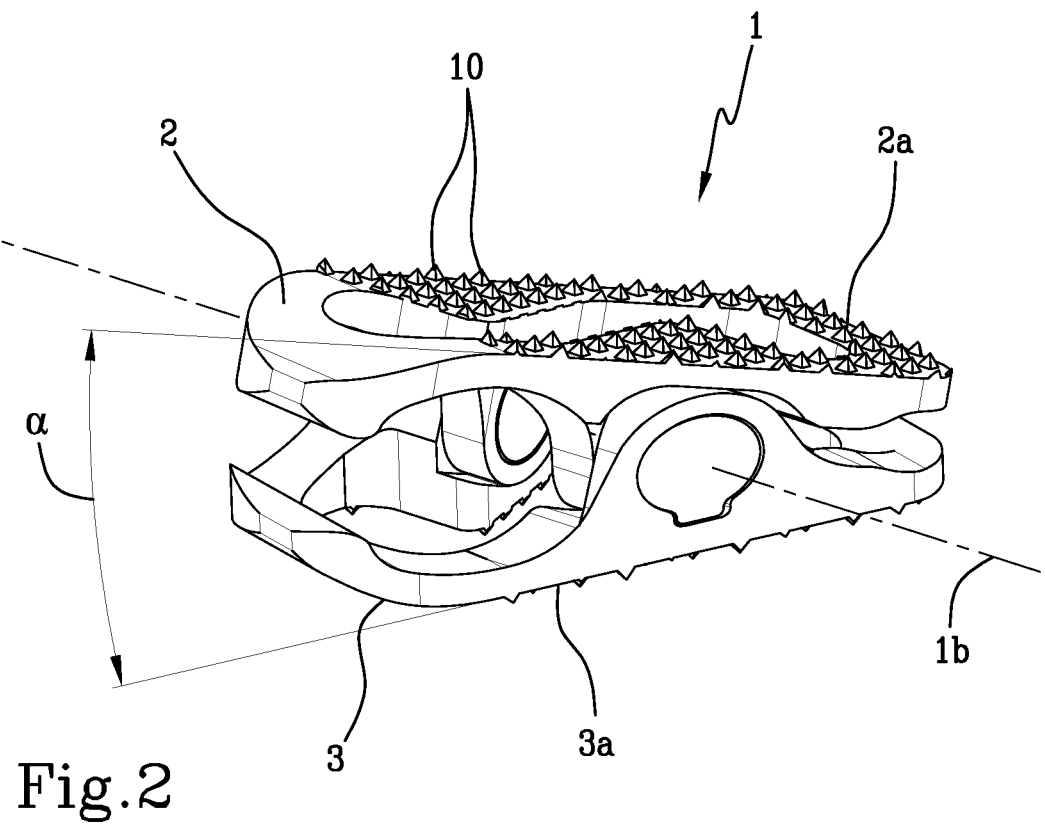
FIG. 2 is a frontal perspective view of the intervertebral fusion cage according to a different inclination angle.
Figure 3:
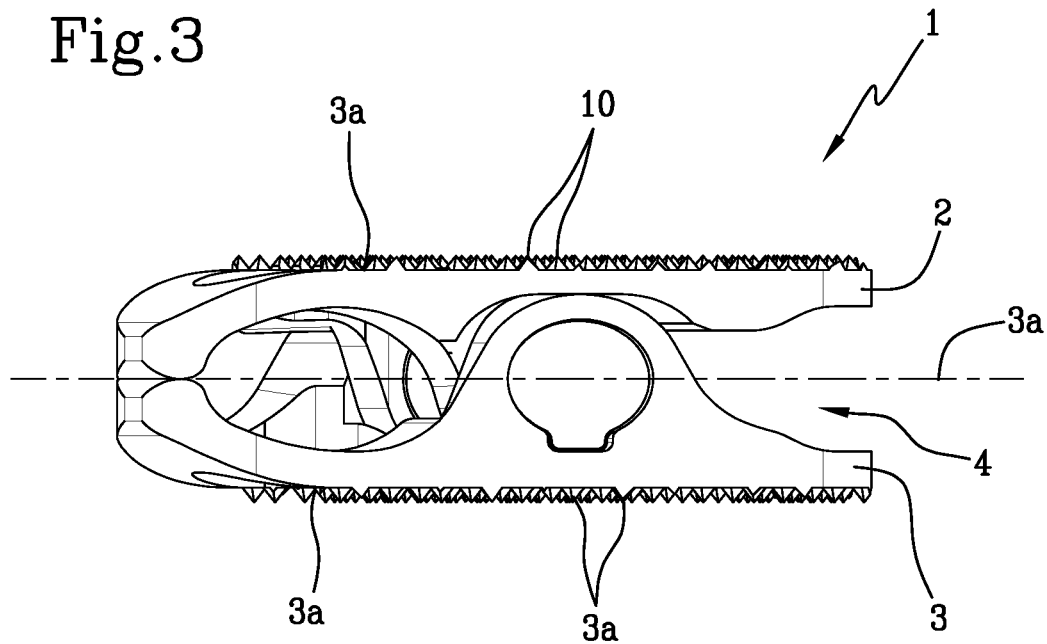
FIG. 3 is a side view of the intervertebral fusion cage according to the present invention.
Figure 4:
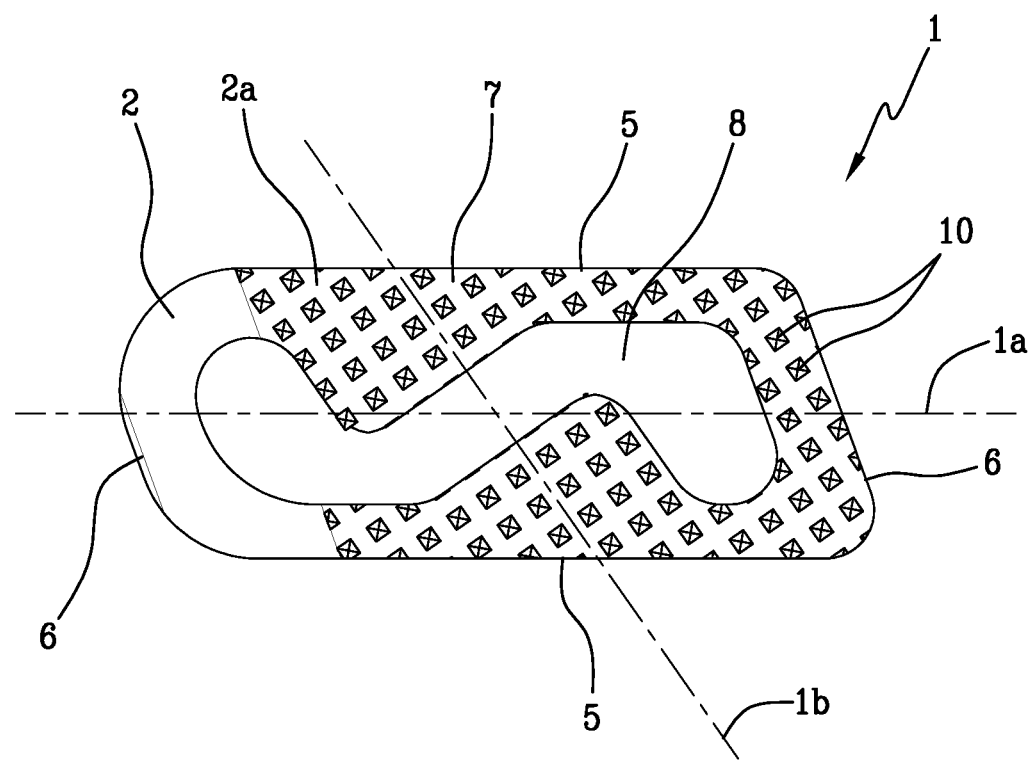
FIG. 4 is a plan view from above of the intervertebral fusion cage according to the present invention.

Advantageously, as illustrated in FIG. 3, the cage 1 has a projectile side profile to facilitate insertion.

The cage 1 also presents a planar shape in the form of a parallelogram. The embodiment illustrated in FIG. 4 foresees two sides 5 parallel to the central axis 1a and two sides 6 oblique in relation to such central axis 1a. An alternative embodiment, illustrated in FIGS. 7 and 8, foresees a rectangular plan.

Of course, configurations of the cage with different plan forms will be possible. Embodiments are illustrated, purely by way of example, in figures from 9 to 11, wherein the cage has an arcuate shaped plan, with both of the larger sides curved (FIG. 9) realizing a sort of arch or C, or a substantially square shape (FIG. 10) or again the shape of a D (FIG. 11).

The planar surface 7 of the first 2 and second 3 portion presents a central slot 8 for the insertion of a bone substitute.

In other words, the surface 7 of each portion 2 and 3 presents a central opening 8 whose extension must be such as to take up most of the plan development of each portion, to facilitate the insertion of a bone substitute, as much as possible, but without weakening the structure of the cage 1 whose contact surfaces 2a and 3a must be such as to allow a correct and stable positioning of the vertebral bodies.

Figure 8:
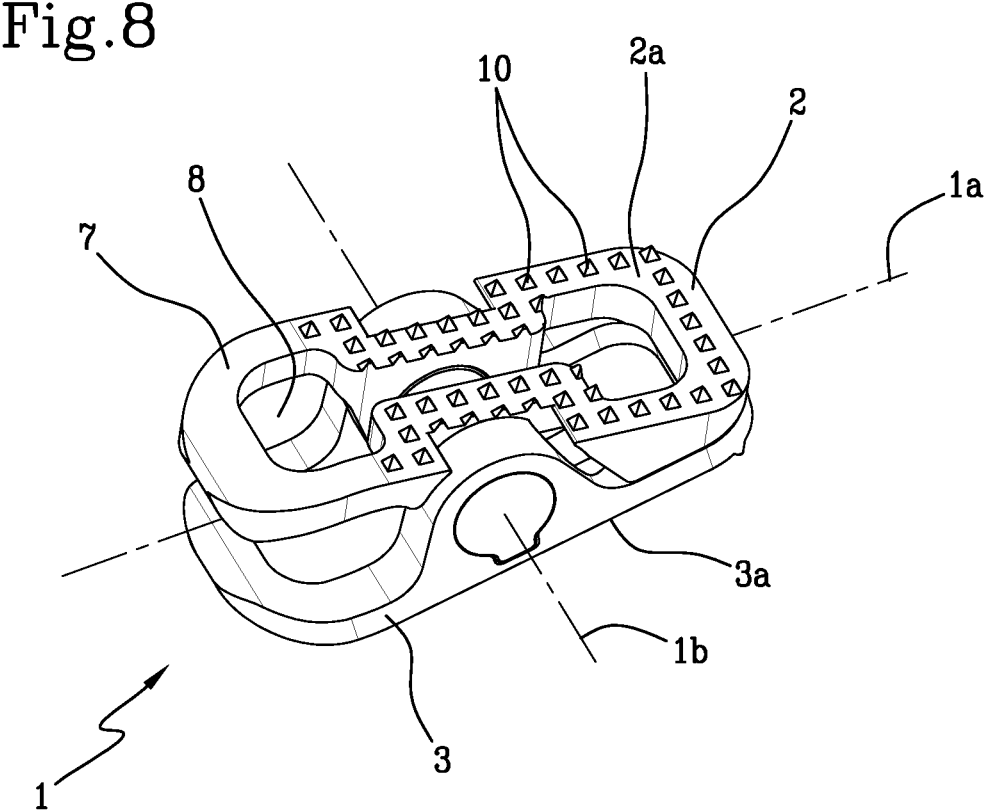

The bone substitute, which serves to promote osteointegration of the cage with the patient's bone structure, can be bone cement or another type of element, such as parts of the patient's bone removed during the operation. In the embodiment illustrated in FIGS. 1-6, such slot 8 is substantially S-shaped, while in the embodiment illustrated in FIG. 7 it presents a rectangular development. The slot can also present other shapes, such as, for example, a double T, as illustrated in FIG. 8, an arch as is visible in FIG. 9, substantially square as in FIG. 10 or again with a double circular sector as shown in FIG. 11.

The fusion cage can also present a gripping area 4 for the connection of the same to a positioning device, neither illustrated nor described in the present patent application.

Figure 5:
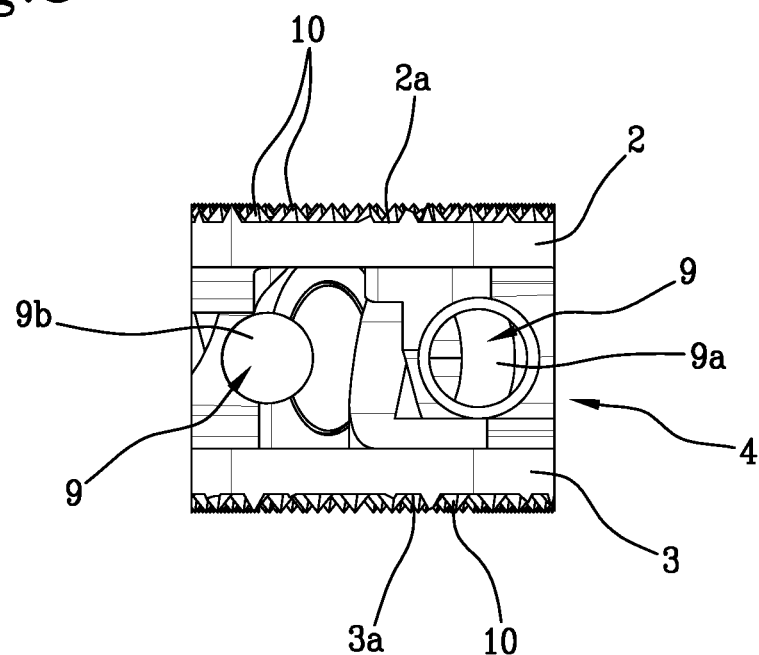
FIG. 5 is a rear perspective view of the intervertebral fusion cage according to the present invention.
Figure 6:
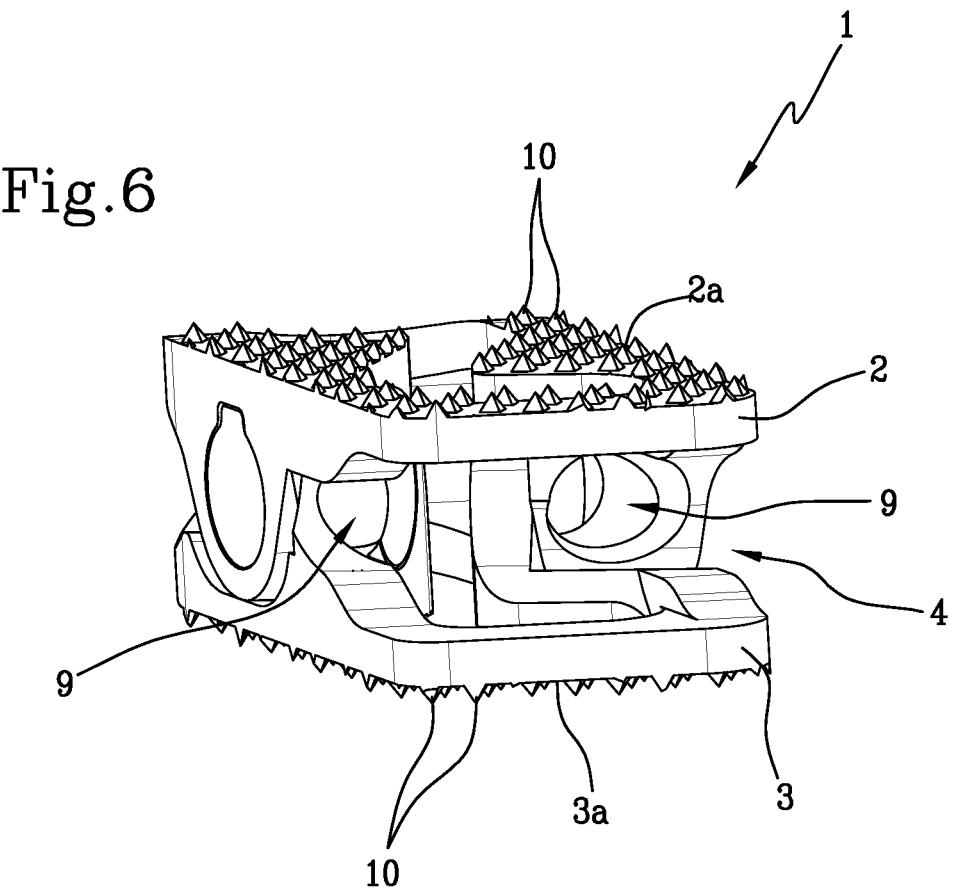
FIG. 6 is a rear view of the intervertebral fusion cage, the subject of the present invention.
Figure 7:
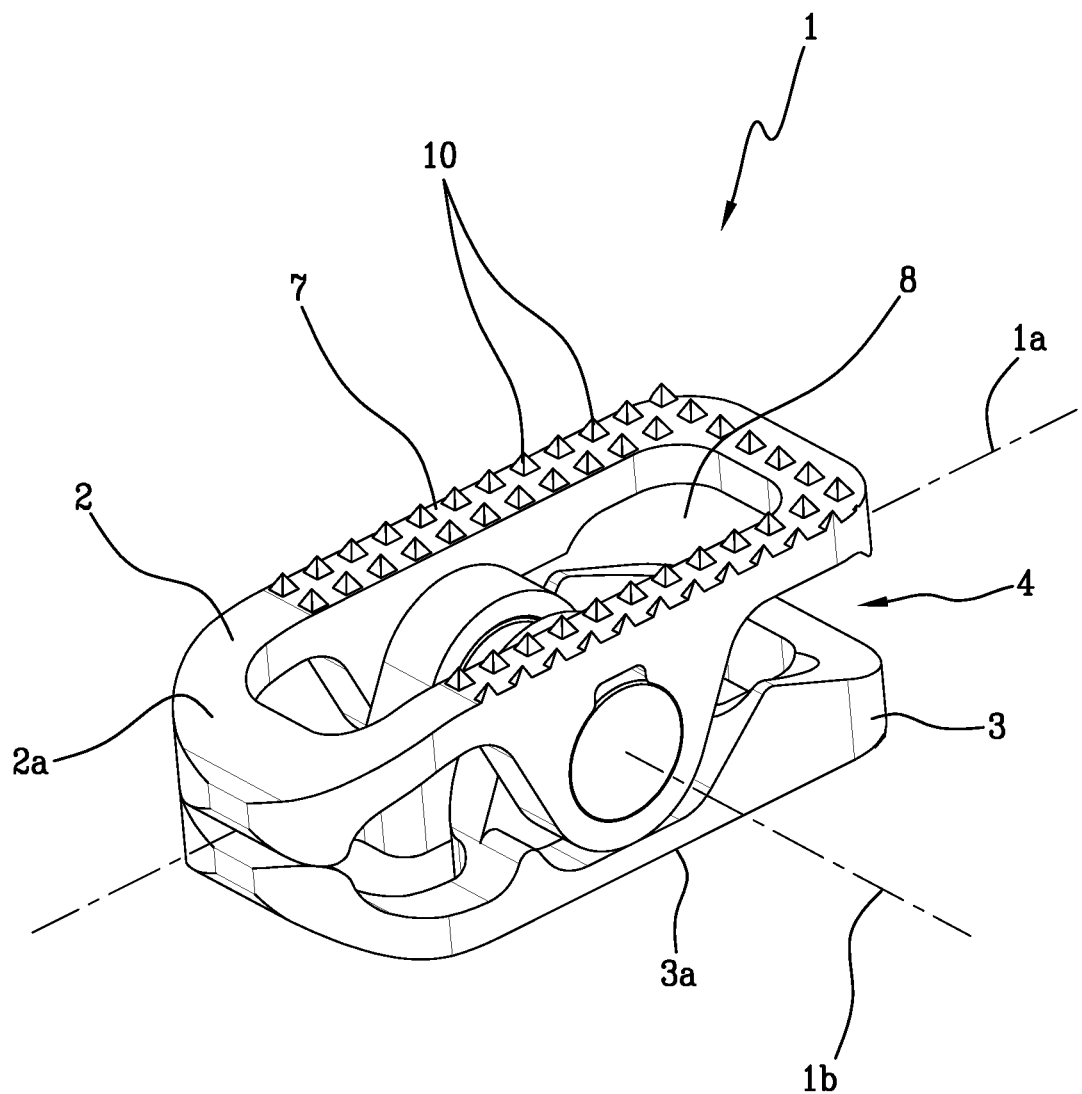
FIGS. 7-11 are frontal perspective views of an intervertebral fusion cage according to the present invention in agreement with different alternative embodiments.

Such gripping area 4, visible in FIGS. 5 and 6, is advantageously placed in a rear area of the cage 1, in particular, along the central axis 1a, in an opposite position to the tip of the projectile shape.

In other words, the gripping area 4 is placed in a distal position in relation to the direction of insertion of the cage 1 between two vertebral bodies.

The gripping area 4 comprises at least one gripping point 9 integral with the first 2 and/or second 3 portion.

In the illustrated configurations, visible in particular in FIGS. 5 and 6, two gripping points 9 are present, one integral with the first portion 2 and the other integral with the second portion 3. It may also be provided that both gripping points 9 are integral with the first portion 2 or both integral with the second portion 3.

The gripping points 9 are preferably holes that can be smooth or threaded internally.

If two gripping points 9 are present, one is preferably threaded 9a and the other is smooth 9b.

The gripping area 4 can also be absent, as shown in FIG. 8, and in this case, the cage is inserted, for example, by means of forceps.

Alternatively, as shown in FIGS. 9 and 11, the gripping area 4, and the relative gripping point 9 is in a lateral position, aligned with the hinge axis 1b.

Whereas, in the configuration in FIG. 10, the gripping area 4 and the relative gripping point 9 are placed at the front.

The invention achieves the proposed set aims as the relative continuous movement between the first and the second portion, and therefore between the two contact surfaces of the intervertebral fusion cage, allow the inclination angle to be varied at will during the operating phase until reaching the inclination angle corresponding to a perfect realignment of the curvature of the vertebral column with what is naturally foreseen.

In this way, the vertebral column does not have to adopt unnatural angles and curvatures, but the cage itself will be guided by the movements and natural curvature of the spine thanks to its continuous movement.

After positioning the cage and choosing the correct inclination angle, the surgeon can proceed with fixing the rest of the implant to the vertebrae by means of external devices, such as clamp rods and polyaxial screws.

Without the rest of the implant, the cage itself would be free to move because only the vertebrae are fixed in the desired position. After identifying the correct curvature of the vertebral column and locking the clamp rods, which immobilise that section of the column, the cage is no longer able to move.

The invention claimed is:

1. An intervertebral fusion cage for the fusion of two vertebral bodies of the vertebral column, comprising a first portion and a second portion opposite the first, both having a planar conformation axially elongated along a central axis, said first and said second portion having respective contact surfaces for receiving, in abutment, a respective vertebral body;
   wherein said first and said second portion are hinged to each other along a hinge axis so as to mutually rotate with a continuous movement;
   wherein said gripping area comprises two gripping points integral with said first and said second portion;
   wherein the two gripping points comprise a threaded gripping point and a smooth gripping point.

2. The cage according to claim 1, wherein said first portion rotates relatively in relation to said second portion by an angle comprised between −40° and +40°.

3. The cage according to claim 1, wherein said first portion rotates relatively in relation to said second portion by an angle comprised between 0° and 40°.

4. The cage according to claim 1, wherein said hinge axis is transversal in relation to said central axis.

5. The cage according to claim 1, wherein, when implanted, said hinge axis lies perpendicularly to the sagittal plane of the patient's body.

6. The cage according to claim 1, wherein the cage has a projectile side profile to facilitate the cage's insertion between two vertebral bodies.

7. The cage according to claim 1, wherein the cage has a planar shape substantially in the form of a parallelogram with rounded or arched corners.

8. The cage according to claim 1, wherein each of said first and said second portions defines a central slot for the insertion of a bone substitute.

9. The cage according to claim 1, wherein the cage comprises a gripping area suitable for being coupled to a respective positioning device for the insertion of said cage inside an intervertebral space.

10. The cage according to claim 9, wherein said gripping area is placed in a rear area of the cage, in a distal position in relation to the direction of insertion.

11. The cage according to 1, wherein a first of the two gripping points is integral with said first portion and a second of the two gripping points is integral with said second portion.

12. The cage according to claim 1, wherein the contact surfaces of said first and said second portion each comprise a plurality of projections suitable for improving the grip between said contact surfaces and said vertebral bodies; said contact surfaces being directed outside the cage itself.

13. The cage according to claim 2, wherein the angle is between −30° and +30°.

14. The cage according to claim 3, wherein the angle is between 0° and 30°.

15. The cage according to claim 9, wherein said gripping area is placed in a side area, along the hinge axis.

* * * * *